United States Patent [19]

Cascione et al.

[11] Patent Number: 5,800,168
[45] Date of Patent: Sep. 1, 1998

[54] ADJUSTABLE GUIDING DEVICE FOR POSITIONING DENTAL IMPLANTS, IMPLANTATION SYSTEM COMPRISING IT AND METHOD EMPLOYING SAME

[76] Inventors: Antonio Cascione, No.18, Via Otranto, 00192 Roma; Luca Relandini, No.173, Via Gigliozzi, 00128 Roma, both of Italy

[21] Appl. No.: 537,921
[22] PCT Filed: May 10, 1994
[86] PCT No.: PCT/IT94/00059
§ 371 Date: Dec. 14, 1995
§ 102(e) Date: Dec. 14, 1995
[87] PCT Pub. No.: WO94/26200
PCT Pub. Date: Nov. 24, 1994

[30] Foreign Application Priority Data

May 14, 1993 [IT] Italy .................. RM93A0316

[51] Int. Cl.$^6$ ............................................. A61C 13/38
[52] U.S. Cl. ................................................... 433/75
[58] Field of Search .......................... 433/75, 76, 214, 433/213, 172, 173, 174; 606/96, 97, 98

[56] References Cited

U.S. PATENT DOCUMENTS

| | | | |
|---|---|---|---|
| 2,724,899 | 11/1955 | Stoll | 433/75 |
| 3,011,259 | 12/1961 | Baum | 433/75 |
| 3,078,580 | 2/1963 | Galvez . | |
| 3,445,935 | 5/1969 | Marshall | 433/75 |
| 4,325,373 | 4/1982 | Slivenko et al. | 433/176 |
| 5,015,183 | 5/1991 | Fenick | 433/76 |
| 5,133,660 | 7/1992 | Fenick | 433/173 |
| 5,320,529 | 6/1994 | Pompa | 433/76 |
| 5,350,297 | 9/1994 | Cohen | 433/76 |
| 5,556,278 | 9/1996 | Meitner | 433/75 |

FOREIGN PATENT DOCUMENTS

| | | |
|---|---|---|
| 0 215 765 | 3/1987 | European Pat. Off. . |
| 2 036 992 | 12/1970 | France . |
| 680 764 | 9/1939 | Germany . |
| 836 993 | 4/1952 | Germany . |

OTHER PUBLICATIONS

English language International Search Report for PCT/IT94/00059.

Primary Examiner—Cary E. O'Connor
Attorney, Agent, or Firm—Beveridge, DeGrandi, Weilacher & Young, LLP

[57] ABSTRACT

A dental implant guiding device and method of use thereof, formed from a radio-opaque tubular guide mounted within the inner member of a radio-transparent support so as to be pivotal about the support's transverse axis and where the inner member is inserted into the outer member and the inner member is translationally shiftable within the outer member so as to permit multi-dimensional positioning adjustment by pivoting the tubular guide and shifting the inner member relative to the outer member, the dental implant guiding device being used in implant surgery and the like where it is important to maintain correct positioning of a dental tool with respect to both the angle of inclination and the vestibule-oral direction. The invention also concerns a method of producing drill templates for implant surgery which makes use of the adjustable guiding device in order to obtain the correct position and orientation of the hole to be drilled in the patient's jaw bone. Further, the invention concerns a kit of instruments and devices for use together with the guiding device in applying said method such as a kit that includes a cylindrical guide housing and a multitude of different sized guide cylinders for receipt in a guide housing fixed in position.

20 Claims, 6 Drawing Sheets

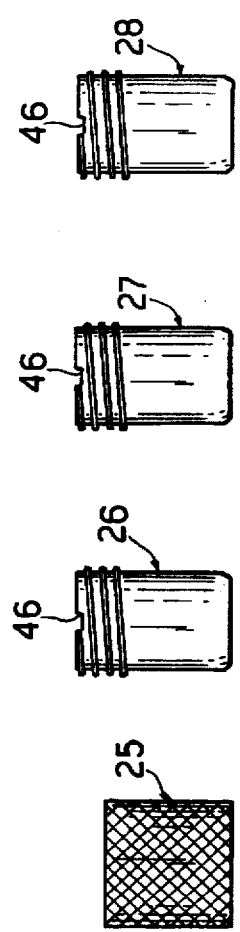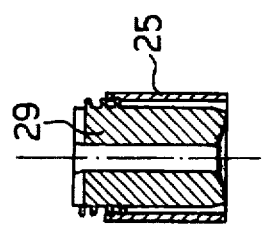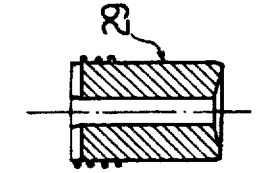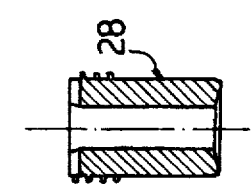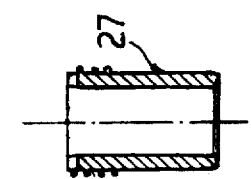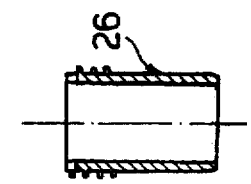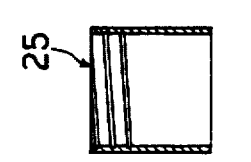

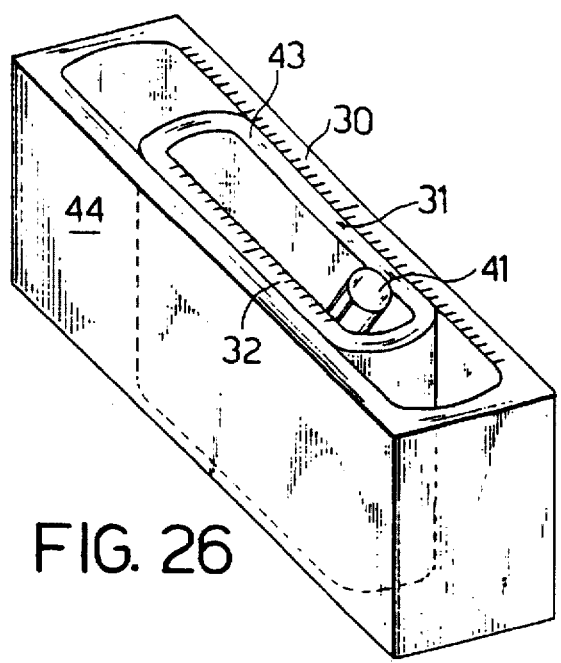
FIG. 26
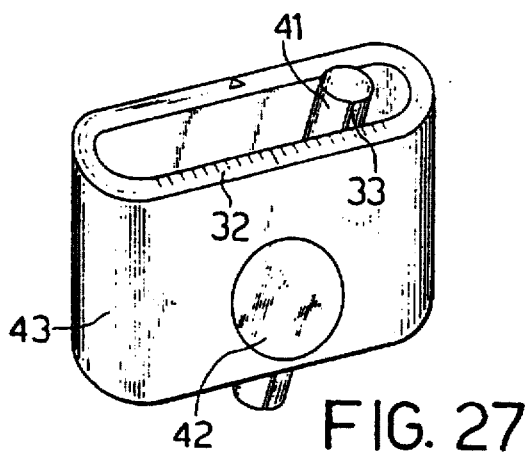
FIG. 27
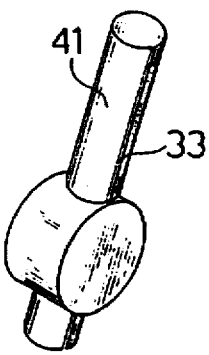
FIG. 28
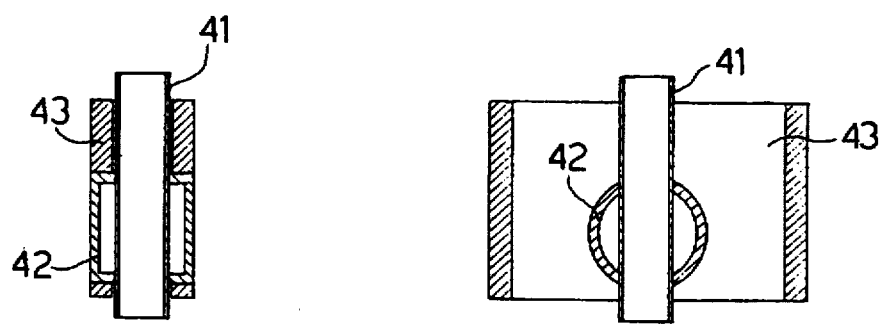
FIG. 29
FIG. 30

ADJUSTABLE GUIDING DEVICE FOR POSITIONING DENTAL IMPLANTS, IMPLANTATION SYSTEM COMPRISING IT AND METHOD EMPLOYING SAME

The present invention relates to the insertion of dental implants in the jaw bones. More particularly, the invention concerns an adjustable guiding device for properly positioning dental implants, an implantation system comprising said device and a method employing the same.

It is well known that fixed dental prostheses such as artificial crowns can be provided by osteointegrated implants, obtained by inserting in the jaw bone tissue an elongated shaft of a suitable material. Said shaft, once implanted, undergoes a process of integration within the bone tissue, and can thus provide a firm support projecting from the gum surface, suitable for connection with a prosthetic element such as an artificial crown.

After having uncovered the bone by removing the gum layer from upon the interested zone the surgical alveolus, i.e. the implant cavity adapted to receive said shaft, is normally obtained in the jaw bone by means of a drilling device. It is extremely important that the hole drilled in the bone tissue has a correct location and inclination with respect to the thickness and morphology of the bone. Care is to be taken to avoid any imperfect fit of the implant, and, most critically, to avoid any perforation of the nearest teeth roots, of the exterior surface of the jaw bone, of the mandibular canal and of the accessory nasal sinuses.

In order to properly direct the drill when making the surgical alveolus, implantologists generally use as a template an acrylic resin mask obtained from a model of the patient's dental arch, adapted to exactly fit over the patient's morsal plane (i.e. the plane lying over the biting surfaces of the teeth). Said mask is provided with a guiding hole in the exact position of the hole to be made or, more preferably, it is provided with a metallic hollow cylinder plunged in the resin in the desired location.

The correct position of the guiding hole or cylinder is determined by the implantologist on the basis of his knowledge and practice, and with the help of a radiographic evaluation of the patient's jaw bone. Once the template is made, however, its configuration cannot be further adjusted. Thus, if the position of the guide in the template, as ascertained by means of X-rays is not correct, a further trial must be made with a new template and further X-rays. In order to avoid further trials or reduce their number, the operator might decide to rely on his skill and experience and empirically modify the direction of the drill forgoing the use of the template.

U.S. Pat. No. 5,015,183 discloses a method for correctly positioning the guiding cylinders or sleeves within a template or stent fitting over the patient's dental arch, which method is carried out with the help of a radio-opaque reference device, comprising a series of regularly spaced radio-opaque wires. Said device is placed in the patients mouth in the site of the missing tooth (or teeth), together with a first stent obtained from a model of the patient's dental arch, bearing another radio-opaque reference wire and X-rays of the patient's jaw bone are taken, thus obtaining a grid of reference points on the resulting radiographic image of the jaw bone section. The optimal direction of the implant seat is determined on the X-ray picture with reference to said radio-opaque grid. After having transversely cut the reference device at a point corresponding to the desired location of the implant, the device is placed on the patient's mouth model and a hole is drilled adjacent to the cut surface of the guiding device, giving to the drill the same inclination as the optimal one determined on the X-ray picture. No guiding means are provided for drilling the pilot hole in the model with the desired inclination, and the latter is obtained by placing the model on a surveying table suitably oriented. After drilling the said hole, a post is inserted therein and a guide cylinder is placed over the post, so that a second stent or template produced on the model will incorporate the guide cylinder in the proper inclination. Any further adjustment of the said inclination is not possible without using a new reference device and making a new template.

Therefore, it is a primary object of the present invention to provide a template with an adjustable drill guide, whose location and inclination can be modified as needed in a precise an reliable way before drilling the implant cavity in the patient's jaw bone without having to repeat the whole construction of the template.

Another object of the invention is to provide a kit or system of instruments for use in dental implant surgery comprising, as the main element, the adjustable drill guide mentioned above, which kit of instruments facilitates the implant surgery and increases the chances of full success thereof.

Yet another object of this invention is to provide a method of producing a drill template for implant cavities which makes use of the said adjustable guide in order to obtain the correct position and orientation of the hole to be drilled in the patients jaw bone.

In accordance with the present invention there is provided a guiding device consisting of a radio-opaque hollow cylinder, preferably made of a metallic material, of the diameter required to guide a drill for implant cavities. rotatably mounted about a transversal axis within a substantially radio-transparent inner support, which support is mounted within an outer substantially radio-transparent support, and can be adjustably displaced relative to the outer support, along a straight line. Thus, the metallic cylinder can be made to change its inclination within the couple of supports by rotating it to about its fixed axis, and can also be shifted lengthwise by displacing the inner support within the outer support.

The guiding device, including the two radio-transparent supports, is of such dimensions as to allow its insertion in the dental arch in place of a missing tooth, with the rotation axis of the guide cylinder substantially parallel to the morsal plane, oriented mesiodistally i.e. lengthwise along the dental arch), and the displacement of the inner support with respect to the outer support having a vestibule-oral direction (i.e., from the labial and buccal surfaces of the teeth to the lingual surfaces thereof, transverse to the mesiodistal direction).

As it will be made clear in the following disclosure, the degrees of freedom of the guide cylinder are such as to allow the position of the hole to be correctly chosen both as concerns its inclination within the jaw bone and as concerns its location in the vestibule-oral direction.

Accordingly, the present invention specifically provides a guiding device for positioning dental implants comprising a tubular guide made of a radio-opaque material, of a size suitable to guide a drill for implant cavities, adapted for being mounted in a template fitting the patient's dental arch or a portion thereof, in the position corresponding to the desired implant location, said guiding device being characterised in that said tubular guide is pivotally connected to a first substantially radio-transparent supporting member so as to be rotatable relative to said first supporting member about an axis orthogonal to the axis of said tubular guide, and in that said first supporting member is adjustably connected to a second substantially radio-transparent supporting member adapted for being fixedly mounted in said template, said first supporting member being shiftable relative to said second supporting member along a straight line orthogonal to said rotation axis.

Further features of the guiding device according to the invention are specified in the enclosed dependent claims.

Once mounted in a suitable template in place of the missing tooth, the guiding device according to the instant invention provides a tubular drill guide which can be both adjustably inclined in a vertical plane having a vestibule-oral direction and adjustably shifted in the same plane, while its outer support is fixedly inserted in the template. Thus, as it will be shown in detail below, the initial position of the metal cylinder of the guide with respect to the jaw bone may be radiographically detected, both its inclination and its location in the vestibule-oral direction may be corrected as required for optimal positioning of the dental implant, and the resulting template with the guiding device may be blocked in the desired position by pouring a suitable filler or glue (such as, e.g., a self-polymerizing resin) in the supports, while leaving the interior of the drill guide cylinder free.

The resulting template, if desired after a further radiographic check, may be directly employed on the patient to obtain the pilot hole in the jaw bone, which hole will have exactly the desired position and inclination. However, as the pilot hole must be enlarged by means of drills of increasing diameter until the chosen implant diameter is reached, the implantologist will have to make sure that this operation is carried out without altering the predetermined inclination of the hole.

In order to assist the operator in executing the surgical alveolus up to its final size, the present invention provides a set of guide cylinders of increasing inner diameter, all fitting into the same cylindrical housing (which may serve as a guide cylinder itself). The housing of the guide cylinders is to be fixedly mounted in the template in place of the guiding device of the invention, while maintaining in the template exactly the same position and inclination of said guiding device, as determined by the previous procedure.

In the event that the above set of cylinders is employed, the guiding device blocked in the desired position is not employed directly on the patient to make the pilot hole, rather it is employed on the plaster model of the patient's dental arch, to obtain a pilot hole with the desired location and inclination, which will serve as a reference for correctly incorporating the housing of the guide cylinders in a suitable template.

Once the latter template is obtained, it may be placed on the patient's dental arch to provide a drill guide of increasing size, starting from the pilot drill, by simply removing guide cylinder from the housing and replacing it with another one.

As pointed out before, the guiding device according to the invention may be adjusted to correct both the inclination of the tubular guide and its location in a vertical plane having a vestibule-oral direction, as, required for optimal positioning of the dental implant. One of the two corrections is brought to the device by displacing the inner supporting member from its initial central position with respect to the outer supporting member, by the required linear distance. The length of this displacement can be measured by means of a reference scale provided along the contact surfaces of inner and outer member, or else it can be easily detected by counting the grooves and ribs provided along said contact surfaces (which should be spaced apart from each other of regular and known distances).

As far as the angular correction is concerned, another suitable scale could be provided on the inner supporting member, parallel to the movement of one tip of the tubular guide with respect to said inner supporting member. However, in order to obtain a more readable measure and a more reliable correction, according to the instant invention an additional instrument may be used, consisting of a sort of goniometer bearing an angular scale on the periphery thereof, and having an elongated pointer pivoted in the rotation center of the angular scale, whose end opposite to the point projects from the lower edge of the instrument. Such head is in the form of a pin sufficiently thin to fit into the tubular guide of the device according to the invention.

By inserting said pin into the tubular guide and sliding said guiding device relative to said instrument along the lower edge of the latter, a rotation is imposed to the tubular guide about its axis, and the angle of the desired inclination is easily read or the scale of the instrument.

As outlined before, the position of the tubular metal guide according to the invention with respect to the patient's jaw bone is detected by means of X-ray techniques, and it is important that the radiographs show as clearly as possible the location and size of the metal cylinder within the patient's mouth. It has been ascertained that in order to obtain a clear image of the cylinder, the X-rays should impact on it from a direction perfectly orthogonal to its geometrical axis. For this reason it is of a critical importance that the patient's head be properly positioned with respect to the X-rays direction.

To that aim, a couple of reference bars or tubes made of a metallic or radiopaque material may be fixedly connected to the labial margin of the template, in such a way as to project outside the patient's mouth when the template is in its proper location in the patient's mouth. Said bars are positioned so as to be parallel to each other, and orthogonal to the geometrical axis of the tubular guide. It will be appreciated that said reference bars provide a reliable means for correctly positioning the tubular guide, by adjusting the position of the patient's head so as to align said bars with the X-rays direction.

Thus, the present invention further provides an implanting system comprising the adjustable guiding device according to the invention, and one or more of the additional devices described above.

The invention further provides a method of producing a drill template for implant cavities which takes advantage from the adjustable guiding device disclosed, as outlined before and as more specifically recited in claims 10 to 14.

A better understanding of the invention can be obtained from the following detailed description of some preferred embodiments thereof when considered in conjunction with the accompanying drawings, wherein:

FIGS. 13 and 14 are respectively a front view and a cross-sectional view of a cylindrical guide housing according to the invention;

FIGS. 15 and 16 are respectively a front view and a cross-sectional view of a first guide cylinder according to the invention;

FIGS. 17 and 18 are respectively a front view and a cross-sectional view of a second such guide cylinder;

FIGS. 19 and 20 are respectively a front view and a cross-sectional view of a third such guide cylinder;

FIGS. 21 and 22 are respectively a front view and a cross-sectional view of a forth such guide cylinder;

FIG. 23 is a front view of an assembly of guide housing and guide cylinder as shown in FIGS. 13 and 21;

FIG. 24 is a cross-sectional view of the assembly shown in FIG. 23;

FIG. 25 is a top plan view of the assembly shown in FIG. 23;

FIG. 26 is a perspective view of a second embodiment of guiding device according to the present invention;

FIG. 27 is a perspective view of the inner supporting member of the guiding device shown in FIG. 26;

FIG. 28 is a perspective view of the rotatable pivot and tubular guide of the supporting member shown in FIG. 27;

FIG. 29 is a first cross-sectional view of the assembly shown in FIG. 28; and

FIG. 30 is a second cross-sectional view of the assembly shown in FIG. 28.

Figure 1:
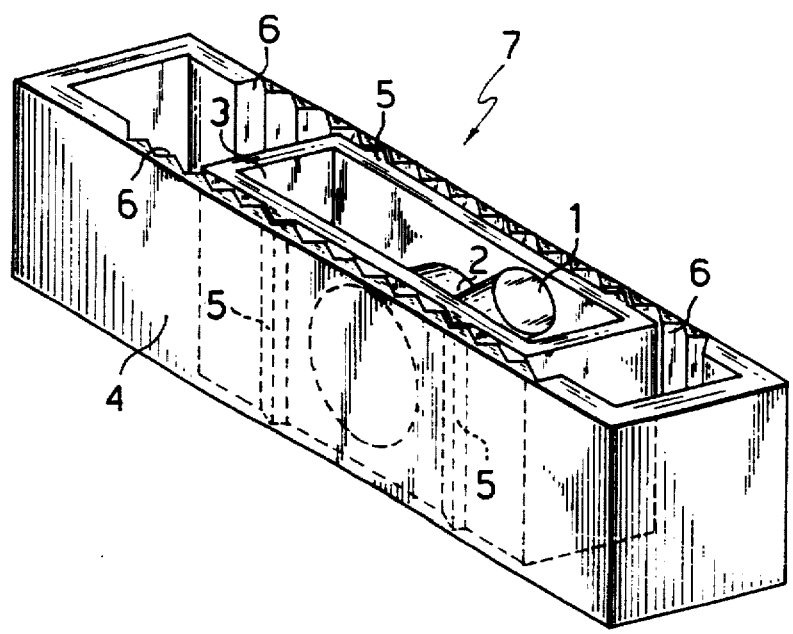
FIG. 1 is a perspective view of a guiding device according to the invention.

A preferred embodiment of the guiding device according to the present invention is shown in FIG. 1. Such device comprises a guide tube (1) made of a radio-opaque material, preferably a metal, whose size is adapted for it to be used as a guide for a relatively thin drill in the preparation of a surgical alveolus. Such drill, which will be chosen in the operation as the pilot drill, may have a diameter of 1–2 mm.

Figure 3:
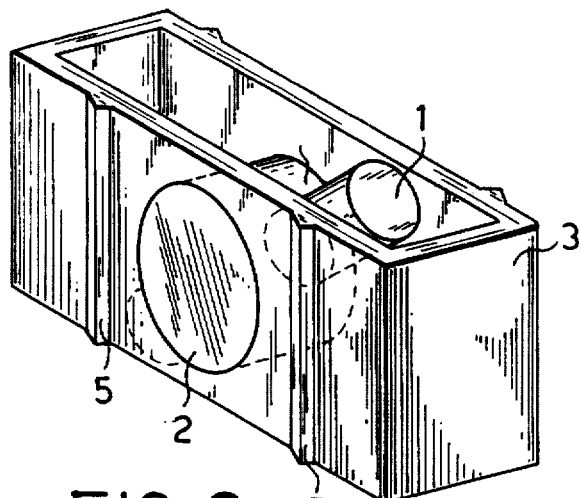
FIG. 3 is a perspective view of the inner supporting member of the guiding device shown in FIG. 1.
Figure 4:
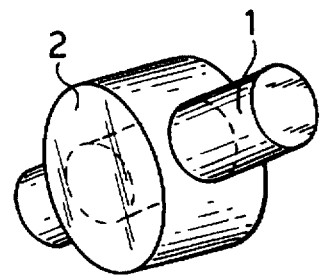
FIG. 4 is a perspective view of the rotatable pivot and tubular guide of the supporting member shown in FIG. 3.
Figure 5:
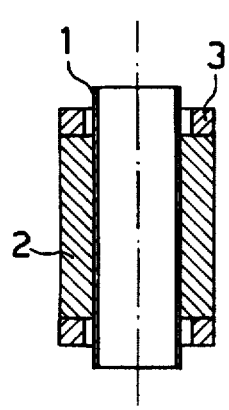
FIG. 5 is a first cross-sectional view of the assembly shown in FIG. 4.
Figure 6:
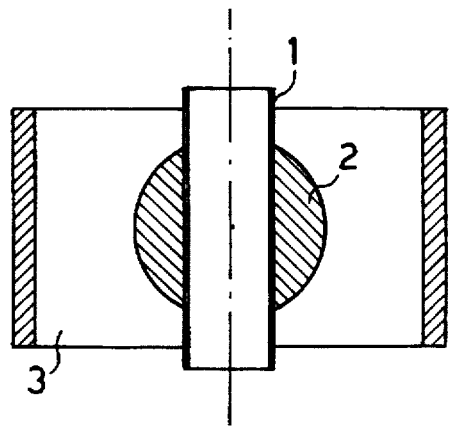
FIG. 6 is a second cross-sectional view of the assembly shown in FIG. 4.

The guide tube (1) is fixedly connected to a pivot (2) (see FIGS. 3–6) which provides a rotation axis to the guide tube (1) when the latter is in place in the assembly shown in FIG. 3. The rotation axis of the guide tube (1) is orthogonal to its geometrical axis, and the pivot (2) is mounted in a substantially parallelepipedal casing (3) by insertion of the pivot (2) across the casing (3), in the centre of two opposite sides thereof.

The parallelepipedal casing (3) is made of a substantially radio-transparent material, e.g. a suitable plastic material, and is open on two opposite sides, so as to allow the guide tube (1) to project above its upper edge and below its lower edge without hindering the rotation thereof about the pivot (2). However, in order to properly function in the method according to the invention, the pivot (2) should rotate with a slight friction in its seat, so that the inclination of the guide tube (1) cannot be inadvertently modified once set. In the embodiment shown in FIGS. 1–6 the pivot (2) is made of a plastic material as well, so that the only radio-opaque element of the assembly-shown in FIG. 3 is the guide tube (1).

As is shown in FIG. 1, the casing (3) is inserted in a second, outer casing (4) open on two opposite sides corresponding to the open sides of the inner casing (3). The outer casing (4) is also parallelepipedal in shape, but has one dimension, i.e. the dimension orthogonal to the rotation axis of the guide-tube (1) and parallel to the two open sides, which is considerably greater than the corresponding dimension of the inner casing (3). On the contrary, on the sides through which the pivot (2) is mounted, the dimension of the inner casing (3) is only slightly smaller than the corresponding dimension of the outer casing (4), so that two opposed contact surfaces are provided between the two latter couples of sides. Thus, the inner casing (3) may be displaced within the outer casing (4) along the direction corresponding to the longest side of the outer casing (4), while remaining in contact with the outer casing (4) through two of its faces.

In the embodiment shown in FIGS. 1–6, the contact between said two couples of surfaces is provided by two series of ribs (5) and grooves (6), running respectively across the outer surface of the inner casing (3) and across the inner surface of the outer casing (4), in a direction orthogonal to the open sides of both casings (3 and 4).

As it may be understood from FIG. 1, the displacement of the outer casing (4) with respect to the inner casing (3) is obtained by extracting the latter from the former and by inserting it again in a different position with respect to the outer casing (4). While it is clear that the inner casing (3) should be easily extracted from the outer casing (4), its is also advisable that a slight friction be present between the ribs (5) and grooves (6), so that the inner casing (3) is not allowed to fall from the assembly if the latter is inadvertently overturned.

The grooves (6) provided on the inner walls of the outer casing (4) are regularly spaced, e.g. by 1 mm, while the ribs (5) on the outer wall of inner casing (3) (see FIG. 3) are only two on each side. By suitably positioning the two series of grooves (6) and the two couples of ribs (5) on the two casings it is possible to obtain a guiding device whose guide tube (1) may be shifted by steps of as less as ½ mm. Such half-pitch shifting may be obtained by rotating the inner casing (3) by 180° after having extracted it from the outer casing (4) and before reinserting it in the latter.

Conventionally, the guide tube (1) is in its zero position as concerns its inclination when the geometrical axis thereof is orthogonal to the planes of the open sides of the two casings (3 and 4), any inclination with respect of said zero position being expressed by angular measures. Further, the guide tube (1) is in its zero position as concerns its linear shift when the inner casing (3) is exactly in the middle of the outer casing (4), and the geometrical axis of the guide tube (1) is in the centre of the series of ribs (6). Said zero positions could be evidenced, if desired, by means of reference signs on the inner and/or outer casing (3 and 4).

Figure 2:
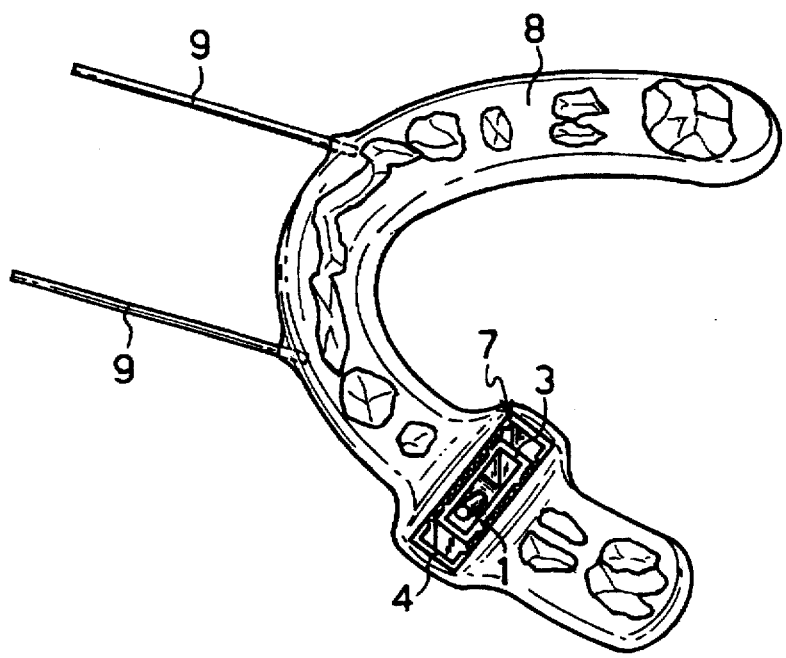
FIG. 2 is a perspective view of a template incorporating the guiding device and the elongate reference members according to the invention.

As shown in FIG. 2, the guiding device (7) shown in FIGS. 1 and 2–6 may be incorporated in a suitable template (8) made from, e.g., an acrylic resin, fitting the patient's dental arch or a section thereof, in a position corresponding to an edentulous site where the desired implant is to be inserted. Thus, as is more readily understood with reference to FIG. 2, the overall dimensions of a guiding device (7) according to the invention should be such as to allow its insertion in place of the smallest possible tooth (front incisor), and such as to allow the patient to fully close his mouth while keeping the template in place, without touching the tips of the guide tube (1). In the event that the latter condition is not fulfilled, the thickness of the whole template (8) will have to be increased as needed.

When producing the template (8) from a model of the patient's dental arch, the guiding device (7) is protected by an easily removable wax filling, in order to prevent any resin from penetrating in the guiding device (7) assembly, thereby hindering its correct adjustment in the subsequent procedure.

FIG. 2 also shows two reference tubes (9) which are preferably included in the system according to the invention, in order to assist in the proper positioning of the patient's head with respect to the X-rays. As pointed out before, the reference tubes (9) are made of a metallic material, in order to be visible in the radiographs, and are connected to the labial margin of the template (8), in such a position to be orthogonal to the guide tube (1).

According to the method of the present invention, the template (8), with the guide tube (1) exactly in the zero position, is put in place in the patient's mouth, and the position of the guide tube (1) with respect to the jaw bone is radiographically evaluated. Before taking the radiograph, the patient is made to move his head until the correct position is reached, as ascertained with the help of the reference tubes (9). Irrespective of the specific technique adopted (e.g. polytomograpy, Dentascan, etc.), the radiographs are intended to show cross-sections of the jaw bone, in the interested zone, taken along the vestibule-oral direction parallel to the geometrical axis of the guide tube (1), together with the guide-tube (1) itself.

Figures 7, 8, 9:
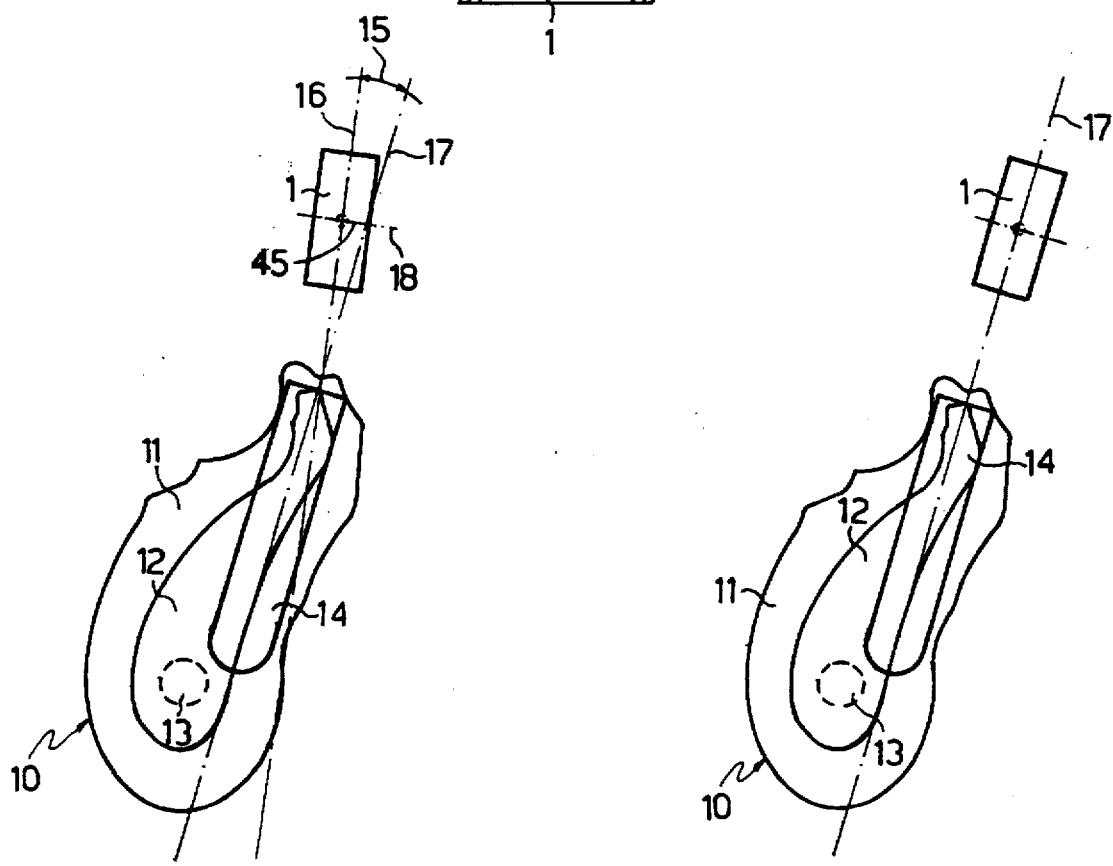
FIG. 7 is a front view of the instrument for rotating the tubular guide according to the invention, also showing a cross-sectional view of the guiding device.
FIGS. 8 and 9 are two schematic views of the jaw bone cross-section, as shown by radiographs, together with the trace of the tubular guide, respectively in the detected and in the desired position.

Said cross-sections, as detected by X-rays, are schematically shown in FIGS. 8 and 9, wherein the jaw bone (10) is outlined as comprising a cortical layer (11) and a medullar layer (12), and as enclosing the mandibular canal (13). FIGS. 8 and 9 also show the outline of the guide tube (1) as detected by X-rays (respectively before and after the adjustment), and the outline of the dental implant (14) chosen for the specific case shown, in the desired position and inclination.

More particularly, FIG. 8 represents the initial situation as detected by the radiographs, with the guide tube (1) in its initial location and inclination (both corresponding to the zero positions in the guiding device according to the invention). As it will be appreciated, in order to be in an optimal position for guiding the drill, as shown by FIG. 9 (i.e., in such a position as to give rise to an implant (14) with the desired location and inclination), the guide tube (1) of the guiding device will have to be both rotated and shifted. The required rotation is such that the geometrical axis (16) of the guide tube (1) becomes parallel to the geometrical axis (17) of the implant (14), and is measured by the angle (15). The required shift is such that the geometrical centre of the rectangle representing the guide tube (1), moving along line (18), falls on the geometrical axis (17) of the implant (14), and is measured by the segment (45).

Obviously, the initial position of the guide tube (1) may be such that one of the above corrections (i.e., rotation and shift) is not necessary. In the event that no correction at all turns out to be necessary, the guiding device according to the invention may be directly blocked with a suitable filling material with the guide tube (1) in its initial position.

The required corrections may be graphically measured, by drawing an outline of the radiographs as shown in FIGS. 8 and 9 and by measuring lengths and angles from the drawing. However, some of the computerized radiographic systems flow available allow to numerically obtain said measures, thus affording easier and more reliable results.

Once measured, said corrections are brought to the guiding device (7), by suitably shifting the inner casing (3) with respect to the assembly of outer casing (4) and template (8), and by rotating the guide tube (1) about the pivot (2). As pointed out before, the rotation of the guide tube (1) by a given angle may be easily effected by means of the instrument shown in FIG. 7, consisting of a sort of goniometer with an angular scale (19) at the periphery thereof and a pointer (20) pivoted in the centre of the angular scale (19). At the opposite end of the pointer (20) there is provided a pin (21) which is insertable in the guide tube (1), as shown by the arrow in FIG. 7. The latter only shows a cross-section of the guiding device, but it is clear that the instrument is normally used on a guiding device (7) incorporated in a template (8).

The above instrument is employed by inserting the pin (21) in the guide tube (1) so that the lower edge (22) of the instrument abuts on the upper edge of the guiding device, and by sliding the instrument with respect to the guiding device (7) while keeping the two elements into close contact with each other. The operation is completed when the angle corresponding to the desired inclination of the guide tube (1) is shown on the angular scale (19) by the pointer (20).

Figure 10:
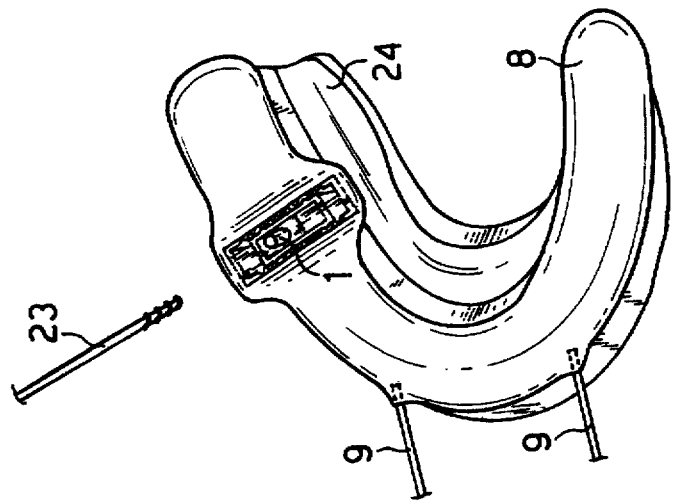
FIG. 10 is a perspective view of a model of the patient's dental arch fitted with a template according to the invention, in one specific phase of the method according to the invention.

Once the location and inclination of the guide tube (1) are set, a suitable filler is poured in the guiding device (7), finally blocking the latter as shown in FIG. 10. In this operation care should be taken not to pour the filler within the guide tube (1), since the latter must be kept free for guiding the drill (23).

In one preferred embodiment of the invention, the template (8) as obtained from the foregoing procedure is not employed on the patient, but is used to obtain a pilot hole on a plaster model (24) of the patient's dental arch. FIG. 10 schematically shows this step.

The pilot hole in the model (24) is then used as a reference for producing a new template—or, as it will be made clear below, for modifying the template (8)—having a cylindrical guide housing (25) in place of the guiding device (7). Said cylindrical guide housing (25) has exactly the position and inclination as determined by means of the guiding device of the invention.

The cylindrical guide housing (25), shown in FIGS. 13 and 14, is an internally threaded hollow metal cylinder which provides a seat for a series of externally threaded metal guide cylinders (26–29) (see FIGS. 15–22). All of the guide cylinders (26–29) have approximately the same outer diameter, as each of them is adapted to be screwed into the guide housing (25), but they have inner holes of different diameter, so as to provide a series of interchangeable guides for drills of different size. In the set shown, the guide cylinder (29) is the one fitting the pilot drill, while the guide of the largest diameter, i.e. 4 mm, is provided by the guide housing (25) itself.

The cylindrical guide housing (25) is knurled on its outer surface, so as to be firmly gripped by the resin of the template (8) in which it is incorporated. In order to be easily screwed in the guide housing (25) as shown in FIGS. 23–25, and to be readily removed therefrom when changing the drill and the guide during the operation, the guide cylinders (26–29) are provided with a slot (46) for engagement with a slot-head screw driver.

Figure 12:
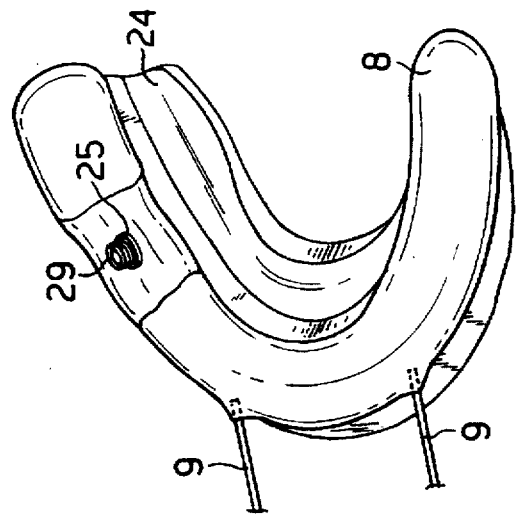
FIG. 12 is a perspective view of the same model shown in FIG. 11, in yet another phase of said method.
Figure 11:
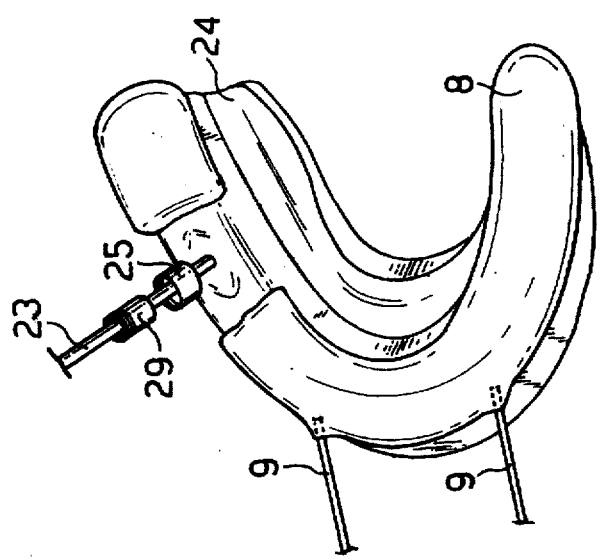
FIG. 11 is a perspective view of the same model shown in FIG. 11, in another phase of said method.

In the method according to the invention, as is shown in FIGS. 11 and 12, the guiding device (7) is cut away from the template (8) after having made the pilot hole in the model (24), the two remaining sections of template (8) are placed again on the model (24), the guide cylinder (29) and the guide housing (25) are fitted on the pilot drill (23), and the latter is inserted in the pilot hole. Then, after having protected the assembly of guide housing (25) and guide cylinder (29) with a suitable wax, the said assembly is joined with the two template sections by pouring the resin around it, so as to reconstitute the template's integrity.

The resulting modified template (8) has the cylindrical guide housing (25) in place of the guiding device (7), placed in the exact location of the desired implant and having the desired inclination. The template (8) may now be placed on the patient's dental arch for carrying out the implant surgery.

FIGS. 26–30 show another embodiment of the guiding device according to the invention, wherein the inner casing (43) and the outer casing (44) have a slightly different shape and the displacement of the former with respect to the latter is realized by frictionally sliding along the slot formed by the walls of the outer casing (44). In this embodiment, a linear scale (30) is provided on the outer casing (44), with a central a reference hack marking the zero, while a pointer (31) is marked on the inner casing (43).

The angular displacement of the guide tube (41) is also detectable directly from the device, as another suitable scale (32) with a central zero reference jack is provided on the inner casing (43), on an edge opposite to that bearing the pointer (31). A longitudinal cut (33) is visible on the guide tube (41) as a reference mark.

In the embodiment shown the pivot (42), instead of being made of a radio-transparent material, is metallic. In view of what set forth in the foregoing, in order to avoid metal artifacts in the radiographs, this version of the device according to the invention should be used only in connection with polytomography techniques.

From the above disclosure it is evident that the possibility of adjusting the position of the drill guide in the template upon a radiographic check, so that it is adapted to guide the drill exactly in the desired position and with the desired inclination, while being advantageous to all operators, is of particular help to less experienced implantologists, as it prevents from any risk of improperly perforating the jaw bone.

Further, the reliability of this method makes it possible to adopt implants of greater length and/or cross section, which are in all cases desirable in order to provide a stronger support to the implanted tooth or bridge.

The present invention has been disclosed with specific reference to some preferred embodiments thereof, but it is to be understood that modifications and changes may be brought to it by those who are skilled in the art without departing from its true spirit and scope.

We claim:

1. A guiding device (7) for positioning dental implants comprising a tubular guide (1, 41) made of a radio-opaque material, of a size suitable to guide a drill (23) for implant cavities, adapted for being mounted in a template (8) fitting the patient's dental arch or a portion thereof, in the position corresponding to the desired implant location, said guiding device (7) being characterised in that said tubular guide (1, 41) is pivotally connected to a first substantially radio-transparent supporting member (3, 43) so as to be rotatable relative to said first supporting member (3, 43) about an axis orthogonal to the axis of said tubular guide (1, 41), and in that said first supporting member (3, 43) is supported by a second substantially radio-transparent supporting member (4, 44) adapted for being fixedly mounted in said template (8), and said second supporting member is dimensioned with respect to said first supporting member (3, 43), such that said first supporting member is repositionable relative to said second supporting member (4, 44) to different drill guide positions along a straight line orthogonal to said rotation axis.

2. A guiding device (7) according to claim 1, wherein said first substantially radio-transparent supporting member (3, 43) is a substantially parallelepipedal casing open on two first opposite sides so as to allow access to said tubular guide (1, 41) mounted therein, said casing (3, 43) bearing a rotatable pivot (2, 42) providing said rotation axis, extending across it between two second opposite sides thereof.

3. A guiding device (7) according to claim 2, wherein said second substantially radio-transparent supporting member (4, 44) is a substantially parallelepipedal casing open on two first opposite sides corresponding to the open sides of said first supporting member (3, 43), and adapted to enclose said first supporting member (3, 43), while providing two opposed inner contact surfaces for contact with the relevant outer surfaces of said first supporting member (3, 43), on the sides corresponding to said two second opposite sides thereof, the length of said second supporting member (4, 44) in the direction orthogonal to said rotation axis and parallel to said open sides being greater than the length of said first supporting member (3, 43) in the same direction enough to allow a proper adjustment of said tubular guide (1, 41) in the vestibule-ral direction.

4. A guiding device (7) according to claim 3, wherein the contact between each of said inner surfaces of said second supporting member (4) and said outer surfaces of said first supporting member (3) is provided by two series of rib and groove engaging means, whereby said ribs (5) and grooves (6) run orthogonal to said open sides, said first supporting member (3) being shiftable relative to said second supporting member (4) by selective engagement of different ribs (5) and grooves (6) of said two series.

5. A guiding device (7) according to claim 3, wherein the contact between each of said inner surfaces of said second supporting member (44) and said outer surfaces of said first supporting member (43) is a friction contact, said first supporting member (43) being shiftable relative to said second supporting member (44) by frictionally sliding it within said second supporting member (43).

6. A dental implantation system comprising a guiding device (7) as defined in claim 1, a cylindrical guide housing (25) adapted for being mounted in a template (8) fitting the patient's dental arch or a portion thereof in the position corresponding to the desired implant location, and a series of interchangeable guide cylinders (26–29), all fitting into said cylindrical housing (25) but each having an axial hole of different diameter.

7. A dental implantation system according to claim 6, further comprising an instrument for rotating of a desired angle said tubular guide (1) about said rotation axis, comprised of a flat support showing an angular scale (19) at the periphery thereof, and having an elongated arm (20) pivoted in the rotation center of said angular scale (19), one end of said arm (20) providing a pointer along said angular scale (19) and the opposed end (21) thereof being insertable into said tubular guide (1) so as to coaxially connect said tubular guide (1) with said pointer.

8. A dental implantation system according to claim 7, wherein said flat support has a straight edge (22) opposed to the edge showing said angular scale (19), said edge being orthogonal to the position of said arm (20) whereby said pointer is on the zero.

9. A dental implantation system according to claim 6, further comprising a couple of elongated straight members (9) made of a radio-opaque material each adapted for being fixedly connected with one end to the labial margin of said template (8).

10. A method of producing a drill template (8) for implant cavities comprising the following steps:
    a) making a template (8) fitting the patient's dental arch or a portion thereof, which template (8) incorporates one or more of the guiding devices (7) according to claim 1 in one or more edentulous jaw sites, each of said guiding devices (7) having the rotation axis of said tubular guide (1, 41) oriented along the mesiodistal line;

b) placing the template (8) produced by step a) in its correct position on the patient's dental arch, with said tubular guide(s) (1, 41) in a reference position both as concerns the inclination and as concerns the shift thereof in the vestibule-oral direction, and obtaining radiographs of the interested jaw sections, taken along the vestibule-oral direction parallel to the geometrical axis of the tubular guide(s) (1, 41), showing said tubular guide(s) (1, 41) as well;

c) for each dental implant to be inserted, considering the desired position (14) of the implant within the jaw bone (10) with the help of said radiographs, and measuring the linear shift (45) and the rotation angle (15) needed to bring the corresponding tubular guide (1, 41) in a position exactly coaxial with the desired position of the implant (14);

d) for each dental implant to be inserted, correcting the vestibule-oral location and inclination of the corresponding tubular guide (1, 41) respectively by the linear shift (45) and by the rotation angle (15) as measured in step c), and blocking said guiding device (7) in the configuration so obtained by pouring a filler or adhesive material within the said supporting members (3, 43, 4, 44), so as to obtain a template (8) with a tubular guide (1, 41) in the desired position and inclination.

11. A method according to claim 10, wherein after step d) the position and inclination of said tubular guide (1, 41) as blocked is further checked radiographically.

12. A method according to claim 10, wherein the template (8) produced by step a) further includes a couple of elongated members (9), fixedly connected with one end to the labial margin of said template (8), both orthogonal to the geometrical axis of said tubular guide (1, 41).

13. A method according to claim 10, wherein the correction of the vestibule-oral inclination of said tubular guide (1) as recited in step d) is carried out by means of an instrument comprising an arm, by inserting an end (21) of said arm (20) in the tubular guide (1) and by sliding said guiding device (7) relative to said instrument along a straight edge (22) thereof until a desired angle (15) is pointed at on a scale (19) of said instrument.

14. A method according to claim 10, further comprising the following steps, for each implant to be inserted:

e) employing the template (8) as obtained from step d) to produce on a model (24) of the patient's dental arch a pilot hole with the desired position and inclination;

f) cutting away from said template (8) a section incorporating said guiding device (7), and placing again on said model (24) the two remaining sections;

g) inserting a guide cylinder (29), fitting a drill (23) employed for said pilot hole, on a drill tip, together with a cylindrical guide housing (25), and inserting the drill (23) with said guide cylinder (29) and housing (25) in the hole obtained from step e);

h) fixedly connecting said guide housing (25), in the position and inclination imposed by the coupling of said drill (23) with said hole, with said two remaining sections of the template, so as to produce a new template (8) having said cylindrical guide housing (25) in place of said guiding device (7).

15. A guiding device (7) for positioning dental implants comprising a tubular guide (1, 41) made of a radio-opaque material, of a size suitable to guide a drill (23) for implant cavities, adapted for being mounted in a template (8) fitting the patient's dental arch or a portion thereof, in the position corresponding to the desired implant location, said guiding device (7) being characterised in that said tubular guide (1, 41) is pivotally connected to a first substantially radio-transparent supporting member (3, 43) so as to be rotatable relative to said first supporting member (3, 43) about an axis orthogonal to the axis of said tubular guide (1, 41), and in that said first supporting member (3, 43) is received within a second substantially radio-transparent supporting member (4, 44) adapted for being fixedly mounted in said template (8) and said first supporting member (3, 43) is releasably retained by said second supporting member to provide for relative adjustment of said first supporting member with respect to said second supporting member (4, 44) to different drill guide positions along a straight line orthogonal to said rotation axis.

16. A guiding device (7) according to claim 15, wherein said first substantially radio-transparent supporting member (3, 43) is a substantially parallelepipedal casing open on two first opposite sides so as to allow access to said tubular guide (1, 41) mounted therein, said casing (3, 43) bearing a rotatable pivot (2, 42) providing said rotation axis, extending across it between two second opposite sides thereof.

17. A guiding device (7) according to claim 16, wherein said second substantially radio-transparent supporting member (4, 44) is a substantially parallelepipedal casing open on two first opposite sides corresponding to the open sides of said first supporting member (3, 43), and adapted to enclose said first supporting member (3, 43), while providing two opposed inner contact surfaces for contact with the relevant outer surfaces of said first supporting member (3, 43), on the sides corresponding to said two second opposite sides thereof, the length of said second supporting member (4, 44) in the direction orthogonal to said rotation axis and parallel to said open sides being greater than the length of said first supporting member (3, 43) in the same direction enough to allow a proper adjustment of said tubular guide (1, 41) in the vestibule-oral direction.

18. A guiding device (7) for positioning dental implants comprising a tubular guide (1, 41) made of a radio-opaque material, of a size suitable to guide a drill (23) for implant cavities, adapted for being mounted in a template (8) fitting the patient's dental arch or a portion thereof, in the position corresponding to the desired implant location, said guiding device (7) being characterised in that said tubular guide (1, 41) is pivotally connected to a first substantially radio-transparent supporting member (3, 43) so as to be rotatable relative to said first supporting member (3, 43) about an axis orthogonal to the axis of said tubular guide (1, 41), and in that said first supporting member (3, 43) is supported by a second substantially radio-transparent supporting member (4, 44) adapted for being fixedly mounted in said template (8), said first supporting member (3, 43) in frictional contact with said second supporting member such that said first supporting member is releasably supported by said second supporting member such that said first supporting member is repositionable relative to said second supporting member (4, 44) to different drill guide positions along a straight line orthogonal to said rotation axis.

19. A guiding device (7) according to claim 18, wherein said first substantially radio-transparent supporting member (3, 43) is a substantially parallelepipedal casing open on two first opposite sides so as to allow access to said tubular guide (1, 41) mounted therein, said casing (3, 43) bearing a rotatable pivot (2, 42) providing said rotation axis, extending across it between two second opposite sides thereof.

20. A guiding device (7) according to claim 19, wherein said second substantially radio-transparent supporting member (4, 44) is a substantially parallelepipedal casing open on two first opposite sides corresponding to the open sides of said first supporting member (3, 43), and adapted to enclose said first supporting member (3, 43), while providing two opposed inner contact surfaces for contact with the relevant outer surfaces of said first supporting member (3, 43), on the sides corresponding to said two second opposite sides thereof, the length of said second supporting member (4, 44) in the direction orthogonal to said rotation axis and parallel to said open sides being greater than the length of said first supporting member (3, 43) in the same direction enough to allow a proper adjustment of aid tubular guide (1, 41) in the vestibule-oral direction.

* * * * *